(12) United States Patent
Smith, Jr. et al.

(10) Patent No.: US 7,977,525 B2
(45) Date of Patent: Jul. 12, 2011

(54) $H_2SO_4$ ALKYLATION BY CONVERSION OF OLEFIN FEED TO OLIGOMERS AND SULFATE ESTERS

(75) Inventors: Lawrence A. Smith, Jr., Pasadena, TX (US); Abraham P. Gelbein, Raleigh, NC (US); William M. Cross, Jr., Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 815 days.

(21) Appl. No.: 12/023,390

(22) Filed: Jan. 31, 2008

(65) Prior Publication Data

US 2009/0198091 A1 Aug. 6, 2009

(51) Int. Cl.
*C07C 2/62* (2006.01)
(52) U.S. Cl. .......................... 585/717; 585/731; 585/730
(58) Field of Classification Search .................. 585/717, 585/730, 731
See application file for complete search history.

(56) References Cited

U.S. PATENT DOCUMENTS

| | | | |
|---|---|---|---|
| 2,762,853 A | 9/1956 | Jones et al. | |
| 2,859,260 A | 11/1958 | Stiles | |
| 3,013,092 A | 12/1961 | Watson et al. | |
| 3,013,093 A | 12/1961 | Stiles | |
| 3,544,652 A * | 12/1970 | Dijk | 585/714 |
| 4,313,016 A | 1/1982 | Manning | |
| 4,540,839 A | 9/1985 | Keyworth et al. | |
| 5,003,124 A | 3/1991 | Smith, Jr. et al. | |
| 6,335,473 B1 | 1/2002 | Bakshi et al. | |
| 6,774,275 B2 | 8/2004 | Smith, Jr. et al. | |
| 6,858,770 B2 | 2/2005 | Smith, Jr. et al. | |
| 6,995,296 B2 | 2/2006 | Smith, Jr. et al. | |

OTHER PUBLICATIONS

"Alkylation of Isobutane with C4 Olefijns. 1. First-Step Reactions Using Sulfuric Acid Catalyst," Lyle F. Albright et al., Ind. Eng. Chem. Res. 1988, 27, 381-386 ["Alkylation of Isobutane with C4 Olefins. 3. Two-Step Process Using Sulfuric Acid Catalyst," Lyle F. Albright et al., Ind. Eng. Chem. Res. 1988, 27, 391-397.] (12 pages).

* cited by examiner

*Primary Examiner* — Thuan Dinh Dang
(74) *Attorney, Agent, or Firm* — Osha • Liang LLP

(57) ABSTRACT

A process for treating an alkylation feedstock comprising olefins, n-alkanes, and iso-alkanes, the process including: contacting at least a portion of the alkylation feedstock with sulfuric acid in a reaction zone under conditions to form sulfate esters of the olefins; separating the n-alkanes and the iso-alkanes from the sulfuric acid and the sulfate esters; recovering the n-alkanes and the iso-alkanes in a first product stream; and recovering the sulfate esters in a second product stream; wherein the sulfuric acid has a strength titrating as below 75 weight percent $H_2SO_4$/water mixtures.

23 Claims, 3 Drawing Sheets

US 7,977,525 B2

H$_2$SO$_4$ ALKYLATION BY CONVERSION OF OLEFIN FEED TO OLIGOMERS AND SULFATE ESTERS

BACKGROUND OF DISCLOSURE

1. Field of the Disclosure

Embodiments disclosed herein relate generally to the alkylation of paraffinic hydrocarbon feedstocks. More particularly, embodiments disclosed herein relate to a process for the preparation of an olefin-containing feed and an alkylation process using the prepared feed.

2. Background

Alkylation is the reaction of paraffins, usually isoparaffins, with an olefin in the presence of a strong acid which produces paraffins, e.g., of higher octane number than the starting materials and which boils in the range of gasolines. In petroleum refining, the alkylation reaction is generally the reaction of a C$_3$ to C$_5$ olefin with isobutane.

In refining alkylations, hydrofluoric or sulfuric acid catalysts are commonly used. For sulfuric acid catalyzed alkylation, low temperature or cold acid processes are favored, minimizing side reactions. In a typical process, the reaction is carried out in a reactor where the hydrocarbon reactants are dispersed into a continuous acid phase.

For example, U.S. Pat. No. 2,762,853 discloses an alkylation process including feeding isoparaffins, such as isobutane or isopentane and C$_2$-C$_5$ monoolefins to an alkylation reactor. The alkylation reaction is catalyzed with sulfuric acid in excess of 88 percent preferably in excess of 96 percent. The alkylation products are then separated into gasoline range components and heavier alkylate products among other finishing processes.

As another example, U.S. Pat. No. 2,859,260 discloses an alkylation process including reacting isoparaffins with olefins in the presence of a sulfuric acid catalyst. The reaction product is then separated to recover a hydrocarbon-rich phase and an acid-rich phase. The hydrocarbon-rich phase is further treated to remove catalyst esters from the hydrocarbon phase, among other downstream operations. Another example of a prior art alkylation process is disclosed in U.S. Pat. No. 3,013,092.

Whereas the above alkylation reactions may occur in a single reactor, Albright et al. disclose a two-step alkylation process in which butyl sulfates or butyl fluorides are formed in the first step and alkylate is produced in the second step. See, for example, "Alkylation of Isobutane with C$_4$ Olefins. 1. First-Step Reactions Using Sulfuric Acid Catalyst," Lyle F. Albright et al., Ind. Eng. Chem. Res. 1988, 27, 381-386 and "Alkylation of Isobutane with C$_4$ Olefins. 3. Two-Step Process Using Sulfuric Acid Catalyst," Lyle F. Albright et al., Ind. Eng. Chem. Res. 1988, 27, 391-397.

Cold acid alkylation feedstocks generally contain both olefins and paraffins, typically in the C$_3$-C$_5$ range. The propane and n-butane in the feed are non-reactive, and build up in the alkylation process, requiring considerable fractionation energy to remove them. In addition, some C$_4$ olefin feeds, such as those produced by dehydration of butanes, may contain aromatic compounds.

Accordingly, there exists a need for a process for decreasing the concentration of inert alkanes in alkylation feedstocks.

SUMMARY OF THE DISCLOSURE

In one aspect, embodiments disclosed herein relate to a process for treating an alkylation feedstock comprising olefins, n-alkanes, and iso-alkanes, the process including: contacting at least a portion of the alkylation feedstock with sulfuric acid in a reaction zone under conditions to form sulfate esters of the olefins; separating the n-alkanes and the iso-alkanes from the sulfuric acid and the sulfate esters; recovering the n-alkanes and the iso-alkanes in a first product stream; and recovering the sulfate esters in a second product stream; wherein the sulfuric acid has a concentration of less than 75 weight percent H$_2$SO$_4$.

In another aspect, embodiments disclosed herein relate to a process for treating a C$_4$-rich alkylation feedstock comprising n-butenes, n-butanes, and iso-butanes, the process including: contacting at least a portion of the alkylation feedstock with sulfuric acid in a reaction zone under conditions to form sulfate esters of the n-butenes; separating the n-butanes and the iso-butanes from the sulfuric acid and the sulfate esters; recovering the n-butanes and the iso-butanes; and recovering the sulfate esters; wherein the sulfuric acid has a strength that titrates as below 75 weight percent H$_2$SO$_4$/water mixtures.

In another aspect, embodiments disclosed herein relate to a process for treating an alkylation feedstock comprising isoolefins, n-olefins, isoalkanes, and n-alkanes, the process including: feeding the alkylation feedstock to an oligomerization reaction zone under conditions of temperature and pressure to oligomerize at least a portion of the isoolefin; separating the oligomers from the unreacted isoolefin, olefins, n-alkanes, and iso-alkanes by fractionation; recovering at least a portion of the unreacted isoolefin, olefins, n-alkanes, and iso-alkanes; and recovering the oligomers; contacting at least a portion of the recovered unreacted isoolefin, olefins, n-alkanes, and iso-alkanes with sulfuric acid in a reaction zone under conditions to form sulfate esters of the olefins; separating the n-alkanes and the iso-alkanes from the sulfuric acid and the sulfate esters; recovering the n-alkanes and the iso-alkanes; and recovering the sulfate esters; wherein the sulfuric acid has a strength that titrates as below 75 weight percent H$_2$SO$_4$/water mixtures.

In another aspect, embodiments disclosed herein relate to a process for treating an alkylation feedstock comprising olefins, n-alkanes, and iso-alkanes, the process including: contacting at least a portion of the alkylation feedstock with hydrofluoric acid in a reaction zone under conditions to form alkyl fluorides of the olefins; separating the n-alkanes and the iso-alkanes from the hydrofluoric acid and the alkyl fluorides; recovering the n-alkanes and the iso-alkanes in a first product stream; and recovering the alkyl fluorides in a second product stream; wherein the hydrofluoric acid has a strength that titrates as below 75 weight percent HF/water mixtures.

Other aspects and advantages will be apparent from the following description and the appended claims.

DETAILED DESCRIPTION

In one aspect, embodiments disclosed herein relate to the alkylation of hydrocarbon feedstocks. More particularly, embodiments disclosed herein relate to a process for the preparation of an olefin-containing feedstocks and an alkylation process using the prepared feed. In particular, embodiments disclosed herein relate to a process for decreasing the concentration of inert components in an alkylation feed stream.

Alkylation feedstocks used in embodiments disclosed herein may include mixtures of various olefins and paraffins. For example, alkylation feedstocks may include $C_1$-$C_5$ paraffins, including n-alkanes and iso-alkanes, and $C_2$-$C_5$ olefins. Olefins may include n-olefins (straight chain olefins), iso-olefins (branched olefins), and mixtures thereof. In some embodiments, alkylation feedstocks may include a $C_3$-$C_5$ light cracked naphtha (LCN) cut.

In certain embodiments, paraffins may include $C_4$ alkanes (n-butane and isobutane), $C_5$ alkanes (n-pentane, neopentane, and isopentane), and mixtures thereof. In other embodiments, olefins may include ethylene, propylene, $C_4$ olefins (such as 1-butene, 2-butene, isobutylene, or mixtures thereof), $C_5$ olefins (such as 1-pentene, 2-pentene, isopentenes, and mixtures thereof), and mixtures thereof.

As mentioned above, the n-alkanes contained in the alkylation feedstocks are non-reactive, and may buildup in the alkylation process, requiring considerable fractionation energy to remove the non-reactive components. Treatment of the feed, as disclosed herein below, may prevent the non-reactive components from entering the alkylation unit.

Treatment of the hydrocarbon feedstock may include steps to remove olefinic compounds from the paraffinic compounds. For example, olefins may be reacted with sulfuric acid or hydrofluoric acid to produce sulfates or fluorides that remain in an aqueous phase. The aqueous phase may then be separated from the paraffins in the hydrocarbon phase. Although described below with respect to sulfuric acid, embodiments of the processes disclosed herein may also be performed with hydrofluoric acid of appropriate concentration.

Figure 1:
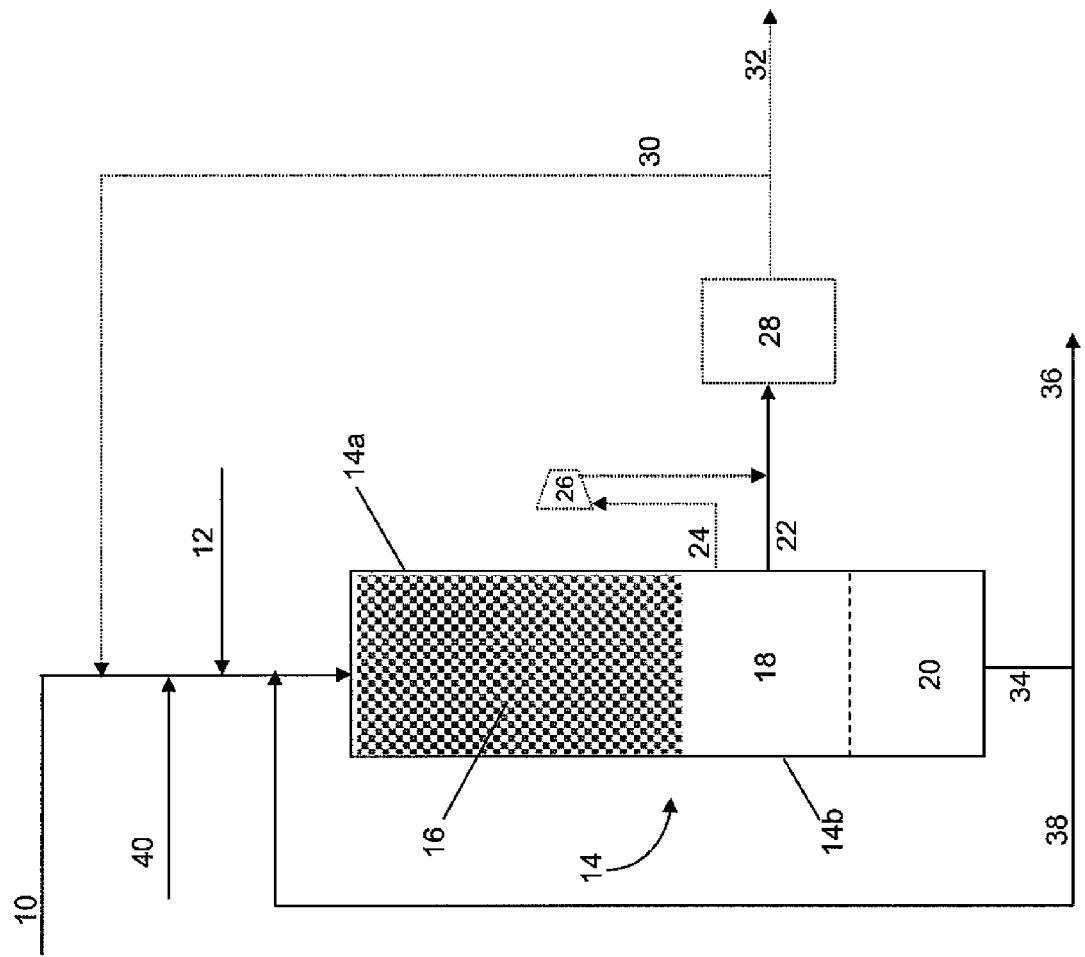
FIG. 1 is a simplified process flow diagram of a process for decreasing the concentration of inert components in alkylation feedstocks, according to embodiments disclosed herein.

Referring to FIG. 1, a simplified process flow diagram of a process for decreasing the concentration of inert components in alkylation feed streams, according to embodiments disclosed herein, is illustrated. Alkylation feedstock 10, including n-olefins, may be contacted with a stream 12, which may include fresh or spent sulfuric acid, in a reactor 14, resulting in a mixed hydrocarbon/acid system.

Reactor 14 may include an upper section 14a and a bottom section 14b. Contact structures 16 may be positioned in upper section 14a to facilitate the intimate contact of the olefins with the sulfuric acid.

Conditions in reactor 14 may be maintained such that at least a portion of the olefins react with the sulfuric acid to form sulfate esters. The reaction mixture may then be separated, for example, by decanting the reaction mixture in lower section 14b to recover a hydrocarbon fraction 18 and an aqueous sulfate ester fraction 20.

Hydrocarbon fraction 18 may be recovered via line 22. Additionally, the heat of reaction may produce some vapors, which may be removed via line 24. If desired, these vapors may be condensed or compressed, such as by using a compressor 26, and combined with the hydrocarbons in line 22.

If desired, the recovered hydrocarbons may pass through a de-entrainment device 28. Additionally, a portion of the recovered hydrocarbons may be recycled via line 30 to the top of reactor 14, such as for purposes of reactor temperature control and to react any unreacted olefin recovered in hydrocarbon fraction 18.

Hydrocarbon fraction 32 may be further processed, such as to separate n-alkanes and iso-alkanes. For example, where a $C_4$ rich alkylation feedstock is treated, recovered n-butane and isobutane may be separated or partially separated, such as in a de-isobutanizer. The de-isobutanizer may be a stand alone unit, or may include a de-isobutanizer that is integrated with pre-treatment processes disclosed herein.

Aqueous sulfate ester fraction 20, which may include sulfate esters and excess acid, may be recovered via line 34. At least a portion of the recovered acid sulfate ester fraction may be recovered and forwarded as alkylation feed to an alkylation unit via line 36.

A portion of acid sulfate ester fraction 20 may also be recycled via line 38, such as to maintain a desired acid concentration in reactor 14a. In some embodiments, the concentration of sulfuric acid phase entering the reactor may be maintained at a concentration that titrates as below 75 weight percent strength sulfuric acid/water mixtures or less. In other embodiments, the sulfuric acid may be maintained at a concentration range titrating as 20 to 50 weight percent sulfuric acid/water mixtures; titrating as 25 to 45 weight percent sulfuric acid/water mixtures in other embodiments; and titrating as 30 to 40 weight percent sulfuric acid/water mixtures in yet other embodiments. It can be noted that that the acid phase in these instances is composed of sulfuric acid, sulfate esters, ASO (acid soluble oils) and water. It does not contain significant quantities of water, typically 0-5% by weight, and for the purposes of describing the acid content, we use the terminology "titrates as" or "titrating as" to indicate a sulfuric acid/water mixture which has the same acidity, understanding that the acid mixture used herein is more complex in chemical makeup. Measurement of the acidity may be measured, for example, using a METTLER DL-77 or a METTLER T-90 titrator.

Stream 12 may include spent sulfuric acid from a cold acid alkylation unit in some embodiments. In other embodiments, stream 12 may include fresh sulfuric acid at an appropriate concentration. In yet other embodiments, additional olefins, such as butenes, pentenes, and mixtures thereof, may be added to reactor 14a via line 40, resulting in additional sulfate esters for use in downstream alkylation processes.

In embodiments where hydrofluoric acid is used to treat the feed, forming alkyl fluorides, the concentration of hydrofluoric acid in the acid phase entering the reactor may be maintained below strengths titrating as 75 weight percent HF/water mixtures. In other embodiments, the hydrofluoric acid may be maintained at a concentration titrating as 20 to 50 weight percent HF/water mixtures; titrating as 25 to 45 weight percent HF/water mixtures in other embodiments; and titrating as 30 to 40 weight percent HF/water mixtures in yet other embodiments.

In some embodiments, alkylation feedstocks that are pre-treated according to embodiments disclosed herein may include iso-olefins. Iso-olefins may polymerize when contacted with sulfuric or hydrofluoric acid, and may result in undesired by-products if such alkylation feedstocks are treated as described with respect to the embodiment of FIG. 1. Alkylation feedstock pretreatment for feedstocks including iso-olefins may be modified to remove the iso-olefins from the feed sent to the sulfate ester reactor or alkyl fluoride reactor. For example, iso-olefins in the alkylation feedstock may be selectively oligomerized to form dimers and trimers of the iso-olefins. These oligomers may then be easily separated from the n-olefins and paraffins. The n-olefins and paraffins may then be separated as described above with respect to FIG. 1, for example. The oligomers and the sulfate esters, individually or in combination, may then be used in a downstream alkylation process.

Figure 2:
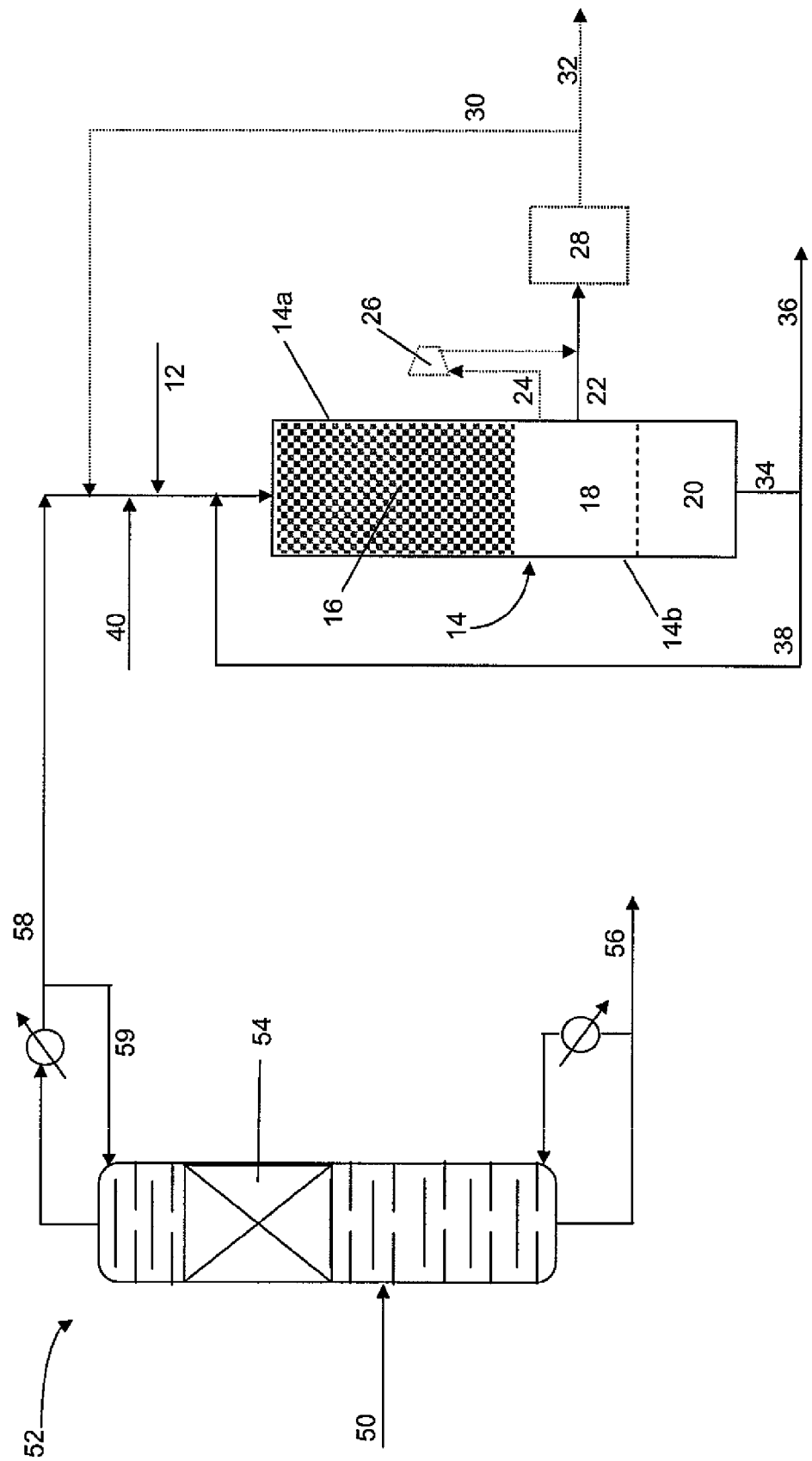
FIG. 2 is a simplified flow diagram of a process for decreasing the concentration of inert components in alkylation feedstocks according to embodiments disclosed herein.
Figure 3:
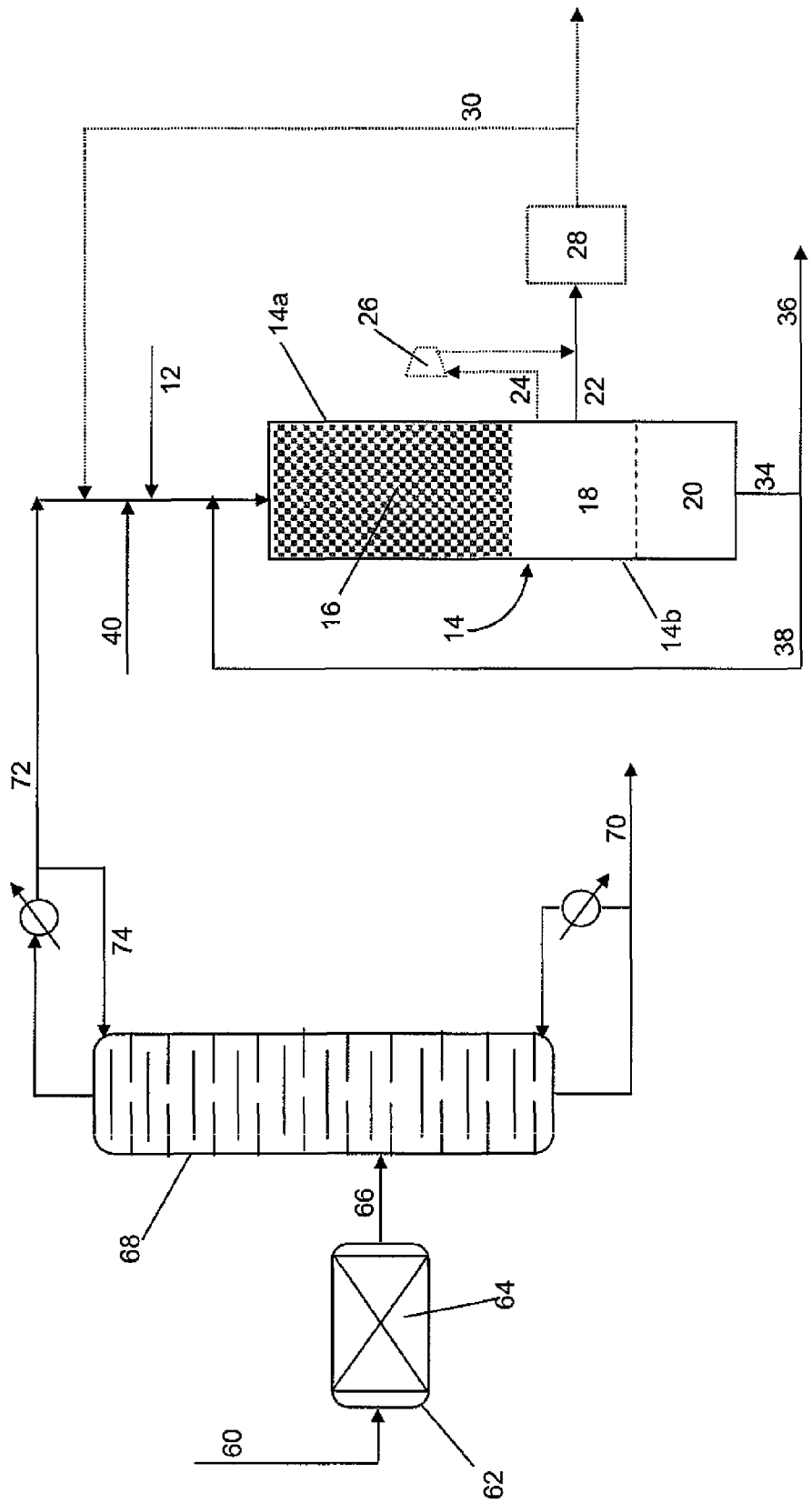
FIG. 3 is a simplified flow diagram of a process for decreasing the concentration of inert components in alkylation feedstocks according to embodiments disclosed herein.

Referring now to FIGS. 2 and 3, where like numerals represent like parts, simplified flow diagrams of processes for decreasing the concentration of inert components in alkylation feedstocks, according to embodiments disclosed herein, are illustrated. In FIGS. 2 and 3, the alkylation feedstock is selectively oligomerized, and the oligomers are separated from the remainder of the alkylation feedstock prior to formation of sulfate esters, as described above.

Referring now to FIG. 2, alkylation feedstock may be fed via line 50 to a distillation column reactor 52 having a catalytic distillation reaction zone 54. The feed may be located above, below or within catalytic distillation reaction zone 54, which may include a catalytic distillation structure for selectively oligomerizing at least a portion of the iso-olefins contained in the alkylation feedstock, resulting in the formation of dimers and trimers of the iso-olefins. Concurrent with the reaction, the oligomers formed, having a significantly greater weight than the paraffins, n-olefins and unreacted iso-olefins, are pushed down the distillation column reactor and recovered as a bottoms fraction via line 56. The paraffins, n-olefins and unreacted iso-olefins may be recovered as an overheads fraction via line 58, a portion of which may be returned to the column as reflux via line 59.

The recovered overheads fraction, containing n-olefins and paraffins, may be treated as described above with respect to FIG. 1 to further separate the n-olefins from the paraffins, resulting in sulfate esters or alkyl fluorides which may be further alkylated, and removing inert components from the alkylation unit feed. The recovered overheads fraction in line 58, including n-olefins, may be contacted with a stream 12, which may include fresh or spent sulfuric acid, in a reactor 14, resulting in a mixed hydrocarbon/acid system.

Conditions in reactor 14 may be maintained such that at least a portion of the olefins react with the sulfuric acid to form sulfate esters. The reaction mixture may then be separated, for example, by decanting the reaction mixture in lower section 14b to recover a hydrocarbon fraction 18 and an aqueous sulfate ester fraction 20.

As above, hydrocarbon fraction 18 may be recovered via line 22, a portion of which may be recycled to the top of reactor 14. Aqueous sulfate ester fraction 20, which may include sulfate esters and excess acid, may be recovered via line 34. At least a portion of the recovered aqueous sulfate ester fraction may be recovered and forwarded as alkylation feed to an alkylation unit via line 36. In some embodiments, recovered sulfate esters in line 36 and recovered oligomers in line 56 are each forwarded to an alkylation unit for further processing.

Referring now to FIG. 3, alkylation feedstock may be fed via line 60 to a fixed bed reactor 62 having a catalytic reaction zone 64. Catalytic reaction zone 64 may include a supported catalyst structure for selectively oligomerizing at least a portion of the iso-olefins contained in the alkylation feedstock, resulting in the formation of dimers and trimers of the iso-olefins. The resulting oligomerized feed may be recovered via line 66 and forwarded to a distillation column 68. The oligomers formed, having a significantly greater weight than the paraffins, n-olefins, and unreacted iso-olefins, are pushed down the distillation column and recovered as a bottoms fraction via line 70. The paraffins, n-olefins and unreacted iso-olefins may be recovered as an overheads fraction via line 72, a portion of which may be returned to the column as reflux via line 74.

The recovered overheads fraction, containing n-olefins and paraffins, may be treated as described above with respect to FIG. 1 to further separate the n-olefins from the paraffins, resulting in sulfate esters or alkyl fluorides which may be further alkylated, and removing inert components from the alkylation unit feed. For example, the recovered overheads fraction in line 74, including n-olefins, may be contacted with a stream 12, which may include fresh or spent sulfuric acid, in a reactor 14, resulting in a mixed hydrocarbon/acid system.

Conditions in reactor 14 may be maintained such that at least a portion of the olefins react with the sulfuric acid to form sulfate esters. The reaction mixture may then be separated, for example, by decanting the reaction mixture in lower section 14b to recover a hydrocarbon fraction 18 and an acid sulfate ester fraction 20.

As above, hydrocarbon fraction 18 may be recovered via line 22, a portion of which may be recycled to the top of reactor 14. Sulfate ester fraction 20, which may include sulfate esters and excess acid, may be recovered via line 34. At least a portion of the recovered sulfate ester fraction may be recovered and forwarded as alkylation feed to an alkylation unit via line 36. In some embodiments, recovered sulfate esters in line 36 and recovered oligomers in line 56 are each forwarded to an alkylation unit for further processing. For example, the oligomer and sulfate may be reacted with isobutane as disclosed in U.S. Pat. Nos. 6,774,275, 6,858,770, and 6,995,296, each of which is incorporated herein by reference.

As described above, FIG. 2 illustrates a process where the iso-olefins are selectively oligomerized and concurrently separated using a catalytic distillation column. FIG. 3 illustrates a process where the iso-olefins are selectively oligomerized and subsequently separated using a distillation column. Other configurations for selectively oligomerizing and separating the iso-olefins from the n-olefins and paraffins are also contemplated, such as use of a distillation column side-reactor.

A reactor that may be used for the reaction of n-olefins with sulfuric acid in some embodiments may include a scaled down version of an alkylation reactor, keeping in mind the requirement for relatively low sulfuric acid concentrations so as to preferentially form sulfate esters and to avoid alkylation of the feed.

In some embodiments, a pulse flow regime may be used for the acid reaction. The pulses may be characterized by large mass and heat transfer rates. Increased contact structure wetting and a continuous mixing between parallel flowing rivulets may diminish flow maldistribution. In addition, the formation of local hot spots may be reduced, leading to an intrinsically safer process. The pulses may continuously mobilize stagnant liquid holdup to the point where its stagnant nature disappears. Since stagnant holdup represents 10 to 30 percent of the total liquid holdup in trickle flow operations, the dynamic character of the pulse flow regime may enhance reactor performance, such as by improved radial mixing.

As described above, contact structures may be positioned in the sulfate ester reactor for contacting the sulfuric acid and a feed stream comprising n-olefins. In some embodiments, contact structures or dispersers used in embodiments described herein may include at least 50 percent void space; at least 60 percent void space in other embodiments; at least 70 percent void space in other embodiments; at least 80 percent void space in other embodiments; and up to 99 percent void space in yet other embodiments. For example, in some embodiments, a contact structure may include a multi-filament component and a structural element, such as a co-knit wire mesh, dispersers, or other suitable contact structures. For example, contact structures as described in U.S. Pat. No. 6,774,275, incorporated herein by reference, may be used.

Reaction of olefins and sulfuric acid to form sulfate ester, as described above, is performed at conditions to preferentially form sulfate esters and to avoid alkylation of the feed, allowing for the separation of the paraffins prior to alkylation. The reactor operating conditions may include reaction temperatures ranging from −30 to 110° F. in some embodiments; ranging from 0 to 40° F. in other embodiments; ranging from 20 to 35° F. in other embodiments; and ranging from 25 to 30° F. in yet other embodiments. Reactor pressures may range from about 5 to about 500 psig in some embodiments; from about 10 to 250 psig in other embodiments; and from about 20 to 150 psig in yet other embodiments. The combination of temperature and pressure used in some embodiments is sufficient to maintain the feed and products in the liquid phase. The esterification may be performed where sulfuric acid is present in at least a stoichiometric ratio to the n-olefin in the reactor feed. In other embodiments, sulfuric acid may be present in a range from about 0.9 to about 1.5 times the stoichiometric ratio; from about 1 to about 1.2 times the stoichiometric ratio in other embodiments; and from about 1 to about 1.1 times the stoichiometric ratio in yet other embodiments.

Comparing the above esterification reaction conditions to those described in the Albright references, it can be readily seen that significantly higher temperatures may be used in embodiments disclosed herein. For example, Albright teaches that lower temperatures are preferred, such as between −20 and −10° C., for the esterification reaction using 96%+ sulfuric acid. In contrast, the inventors have surprisingly found that sulfate ester formation according to embodiments disclosed herein may be conducted at significantly higher temperatures, requiring less refrigeration.

Oligomerization, as described above, may be carried out, for example, in a partial liquid phase in the presence of an acid cation resin catalyst, either in straight pass type reaction, such as that disclosed in U.S. Pat. Nos. 4,313,016, 4,540,839, 5,003,124, and 6,335,473, or in a catalytic distillation reaction where there is both a vapor and a liquid phase and a concurrent reaction/fractionation. Iso-olefins that may be oligomerized may include isobutene, isopentenes (isoamylenes), and combinations thereof, which are more reactive than n-olefins, and are selectively oligomerized.

The primary oligomer products are dimers and trimers of iso-olefins. For example, isobutene may be oligomerized to form a $C_8$ or $C_{12}$ tertiary olefin, isopentene may be oligomerized to form a $C_{10}$ or $C_{15}$ tertiary olefin, and mixtures of isobutene and isopentene may be selectively reacted to form $C_9$, $C_{13}$, and $C_{14}$ tertiary olefins, among other products. During subsequent alkylation, these oligomers react with iso-alkane to form alkylate products, such as isooctane, isononane, and isodecane, among others. Instead of the expected reaction between the oligomer and the isoalkane, the oligomer is cracked into its olefin components, that is, the constituent olefins which reacted to form the oligomers, which react with the isoalkane on a molar basis. The result is the same product as alkylation of the mono-olefin alone with the additional benefit of a less exothermic overall alkylation reaction, which may require less refrigeration and a lower energy cost for the alkylation.

Embodiments of the processes described herein may provide for lower overall energy consumption, separating alkanes and olefins as pretreatment to an alkylation feedstock. This may be accomplished by reacting the olefins to form dimers and/or sulfate esters, which are easier to separate from the alkane fraction. Embodiments disclosed above may provide for the pretreatment of alkylation feedstocks to separate alkanes from olefins using oligomerization, production of sulfate esters, or a combination thereof. Advantageously, embodiments disclosed herein may provide for the separation (decrease in concentration or removal) of inert alkanes from alkylation feedstocks. In other embodiments, processes disclosed herein may provide for alkane-free esters and oligomers for use in alkylation. The resulting oligomers and sulfate esters may then be used in an alkylation unit to produce alkylate.

Advantageously, some embodiments disclosed herein may allow for increased alkylation unit efficiency, resulting from a decreased concentration of inert components. In some embodiments, less acid may be consumed during the alkylation reaction. The increased efficiency may allow for increased reactor throughput for existing alkylation reactors. The increased efficiency may also allow for use of smaller alkylation reactors for newly constructed units.

Additionally, some embodiments disclosed herein may allow for decreased separation costs. Removal of inert components prior to alkylation may decrease or remove the need for downstream separations to recover the inert n-alkanes. Decreased separation costs may be realized, for example, by integrating the n-alkane/iso-alkane separation with existing processes, as opposed to including a stand alone n-alkane/iso-alkane separation unit associated with the alkylation process. Further, embodiments disclosed herein may provide a beneficial use for spent sulfuric acid.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for treating an alkylation feedstock comprising olefins, n-alkanes, and iso-alkanes, the process comprising:
    contacting at least a portion of the alkylation feedstock with sulfuric acid in a reaction zone under conditions to form sulfate esters of the olefins;
    separating the n-alkanes and the iso-alkanes from the sulfuric acid and the sulfate esters;
    recovering the n-alkanes and the iso-alkanes in a first product stream; and
    recovering the sulfate esters in a second product stream;
    wherein the sulfuric acid has a strength that titrates as below 75 weight percent $H_2SO_4$/water mixtures.

2. The process of claim 1, wherein the separating comprises decanting.

3. The process of claim 1, wherein the sulfuric acid has a strength that titrates as 30 to 40 weight percent $H_2SO_4$/water mixtures.

4. The process of claim 1, wherein the contacting is at a temperature in the range from 0° F. to 40° F.

5. The process of claim 1, further comprising feeding at least a portion of the recovered sulfate esters to an alkylation reactor.

6. The process of claim 1, wherein the olefins comprise isoolefin, the process further comprising:
    feeding the alkylation feedstock to an oligomerization reaction zone under conditions of temperature and pressure to oligomerize at least a portion of the iso-olefin;
    separating the oligomers from the unreacted iso-olefin, olefins, n-alkanes, and iso-alkanes by fractionation;
    recovering at least a portion of the unreacted iso-olefin, olefins, n-alkanes, and iso-alkanes for the contacting; and
    recovering the oligomers.

7. The process of claim 6, further comprising feeding at least a portion of the recovered oligomers to an alkylation reactor.

8. The process of claim 6, wherein the iso-olefin comprises at least one of C4 iso-olefins, C5 iso-olefins, and mixtures thereof.

9. The process of claim 6, wherein the oligomers comprise dimers and trimers of the iso-olefin.

10. The process of claim 1, further comprising recycling at least a portion of the recovered iso-alkane and n-alkane to the reaction zone.

11. The process of claim 1, further comprising separating the recovered n-alkanes and iso-alkanes to form an iso-alkane-rich fraction and an n-alkane-rich fraction.

12. The process of claim 1, wherein the olefins comprise $C_3$-$C_5$ olefins, $C_3$-$C_5$ n-alkanes, and $C_3$-$C_5$ iso-alkanes.

13. A process for treating a $C_4$-rich alkylation feedstock comprising n-butenes, n-butanes, and iso-butanes, the process comprising:
   contacting at least a portion of the alkylation feedstock with sulfuric acid in a reaction zone under conditions to form sulfate esters of the n-butenes;
   separating the n-butanes and the iso-butanes from the sulfuric acid and the sulfate esters;
   recovering the n-butanes and the iso-butanes; and
   recovering the sulfate esters;
   wherein the sulfuric acid has a strength that titrates as below 75 weight percent $H_2SO_4$/water mixture.

14. The process of claim 13, wherein the separating comprises decanting.

15. The process of claim 13, wherein the sulfuric acid has a strength that titrates as 30 to about 40 weight percent $H_2SO_4$/water mixtures.

16. The process of claim 13, wherein the contacting is at a temperature in the range from 0° F. to 40° F.

17. The process of claim 13, further comprising feeding at least a portion of the recovered sulfate esters to an alkylation reactor.

18. The process of claim 13, wherein the alkylation feedstock further comprises isobutene, the process further comprising:
   feeding the $C_4$-rich alkylation feedstock to an oligomerization reaction zone under conditions of temperature and pressure to oligomerize at least a portion of the isobutene;
   separating the isobutene oligomers from the unreacted isobutene, n-butenes, n-butanes, and iso-butanes by fractionation;
   recovering at least a portion of the unreacted isobutene, n-butene, n-butanes, and iso-butanes for the contacting; and
   recovering the isobutene oligomers.

19. The process of claim 18, further comprising feeding at least a portion of the recovered isobutene oligomers to an alkylation reactor.

20. The process of claim 13, further comprising recycling at least a portion of the recovered iso-butane and n-butane to the reaction zone.

21. The process of claim 13, further comprising separating the recovered n-butanes and iso-butanes to form an iso-butane-rich fraction and an n-butane-rich fraction.

22. A process for treating an alkylation feedstock comprising isoolefins, n-olefins, isoalkanes, and n-alkanes, the process comprising:
   feeding the alkylation feedstock to an oligomerization reaction zone under conditions of temperature and pressure to oligomerize at least a portion of the isoolefin;
   separating the oligomers from the unreacted isoolefin, olefins, n-alkanes, and iso-alkanes by fractionation;
   recovering at least a portion of the unreacted isoolefin, olefins, n-alkanes, and iso-alkanes; and
   recovering the oligomers
   contacting at least a portion of the recovered unreacted isoolefin, olefins, n-alkanes, and iso-alkanes with sulfuric acid in a reaction zone under conditions to form sulfate esters of the olefins;
   separating the n-alkanes and the iso-alkanes from the sulfuric acid and the sulfate esters;
   recovering the n-alkanes and the iso-alkanes; and
   recovering the sulfate esters;
   wherein the sulfuric acid has a strength that titrates as below 75 weight percent $H_2SO_4$/water mixtures.

23. The process of claim 22, further comprising feeding at least a portion of the recovered olefins and at least a portion of the recovered sulfate esters to an alkylation reactor.

* * * * *